(12) United States Patent
La Casce et al.

(10) Patent No.: US 9,716,125 B2
(45) Date of Patent: Jul. 25, 2017

(54) IMAGING ARRAY AND METHOD FOR SUPPORTING AUTOMATIC EXPOSURE CONTROL IN A RADIOGRAPHIC SYSTEM

(71) Applicant: Varex Imaging Corporation, Salt Lake City, UT (US)

(72) Inventors: Carl La Casce, Park City, UT (US); Richard E Colbeth, Los Altos, CA (US); Ivan P Mollov, Mountain View, CA (US)

(73) Assignee: Varex Imaging Corporation, Salt Lake City, UT (US)

( * ) Notice: Subject to any disclaimer, the term of this patent is extended or adjusted under 35 U.S.C. 154(b) by 142 days.

(21) Appl. No.: 13/724,969

(22) Filed: Dec. 21, 2012

(65) Prior Publication Data

US 2014/0175297 A1    Jun. 26, 2014

(51) Int. Cl.
  *H01L 27/146*  (2006.01)
  *A61B 6/00*    (2006.01)

(52) U.S. Cl.
  CPC ........ *H01L 27/14658* (2013.01); *A61B 6/542* (2013.01); *H01L 27/14659* (2013.01); *A61B 6/4233* (2013.01)

(58) Field of Classification Search
  CPC ... H05G 1/38; H05G 1/44; H05G 1/46; H01L 27/14609
  USPC .................................................... 250/370.09
  See application file for complete search history.

(56) References Cited

U.S. PATENT DOCUMENTS

| 6,404,851 | B1 * | 6/2002 | Possin et al. ............... 378/98.7 |
| 7,002,408 | B2 | 2/2006 | Roos et al. |
| 7,180,366 | B2 | 2/2007 | Roos et al. |
| 2011/0249791 | A1 | 10/2011 | Wang et al. |

FOREIGN PATENT DOCUMENTS

| JP | 2004251892 A | 9/2004 |
| JP | 2011010870 A | 1/2011 |
| KR | 10-2010-0004949 A | 1/2010 |
| WO | 2008063359 A2 | 5/2008 |

OTHER PUBLICATIONS

International Search Report and Written Opinion dated Apr. 10, 2014 issued in connection with PCT/US2013/075715, 10 pages.
International Preliminary Report on Patentability filed in PCT/US2013/075715, issued Jun. 23, 2015, 6 pages.

* cited by examiner

*Primary Examiner* — David J Makiya
*Assistant Examiner* — Kenneth J Malkowski
(74) *Attorney, Agent, or Firm* — Banner & Witcoff, Ltd.

(57) ABSTRACT

An imaging array with integrated circuitry for supporting automatic exposure control and a method for using such an imaging array are provided. One or more electrodes are disposed substantially parallel with at least a portion of the array of pixels forming the imaging array and provide capacitively coupling to at least one photodiode electrode.

10 Claims, 12 Drawing Sheets

FIG. 1

(Prior Art)

(Prior Art)

IMAGING ARRAY AND METHOD FOR SUPPORTING AUTOMATIC EXPOSURE CONTROL IN A RADIOGRAPHIC SYSTEM

BACKGROUND

The present invention relates to radiographic imaging systems using flat panel imaging arrays, and in particular, to such systems having automatic exposure control (AEC) sensing capability.

Figure 1:
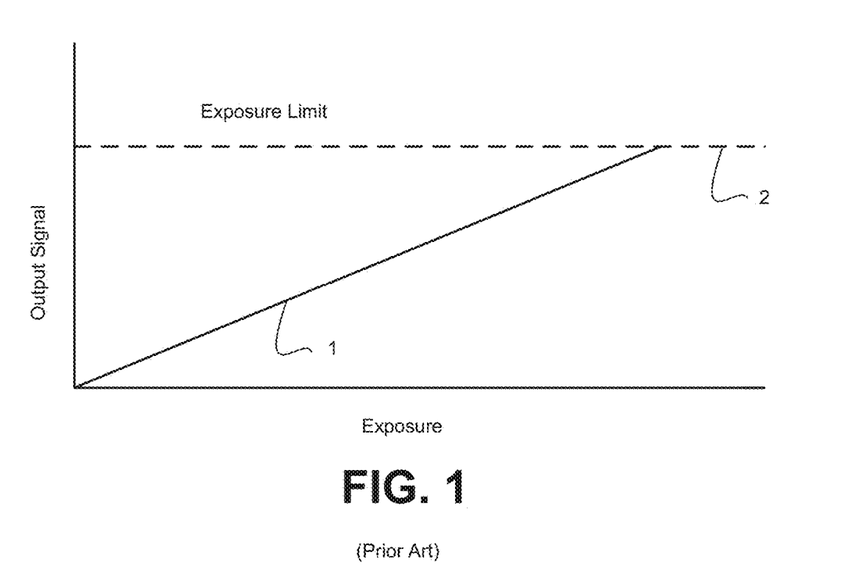
FIG. 1 depicts an output signal level versus exposure level characteristic of an automatic exposure control signal.

Referring to FIG. 1, AEC is used in radiography to control the x-ray dosage delivered to the receptor. Typically, a sensor, separate from the image acquisition devise itself, is positioned in front of or behind the receptor, and senses the x-ray exposure in real time. The AEC device provides an output signal 1 in real time, usually in the form of an analog voltage that is proportional to the total delivered x-ray exposure. This signal 1 is used by x-ray source to terminate the exposure when the signal 1 identifies the exposure as having reached a predefined threshold 2.

Ideally, it would be desirable to use the receptor itself to sense the exposure and provide the AEC signal in real time. However, using the actual image acquisition device itself is problematic for the reason that it is intended to capture the signal on a frame-by-frame basis, and not in real time. For example, in flat panel digital radiography, the exposure is integrated on each pixel and then read out, typically, every few seconds. The x-ray beam duration is defined in tens of milliseconds, so real time in this context would require millisecond or sub-millisecond updates to the total AEC signal value.

Figure 2:
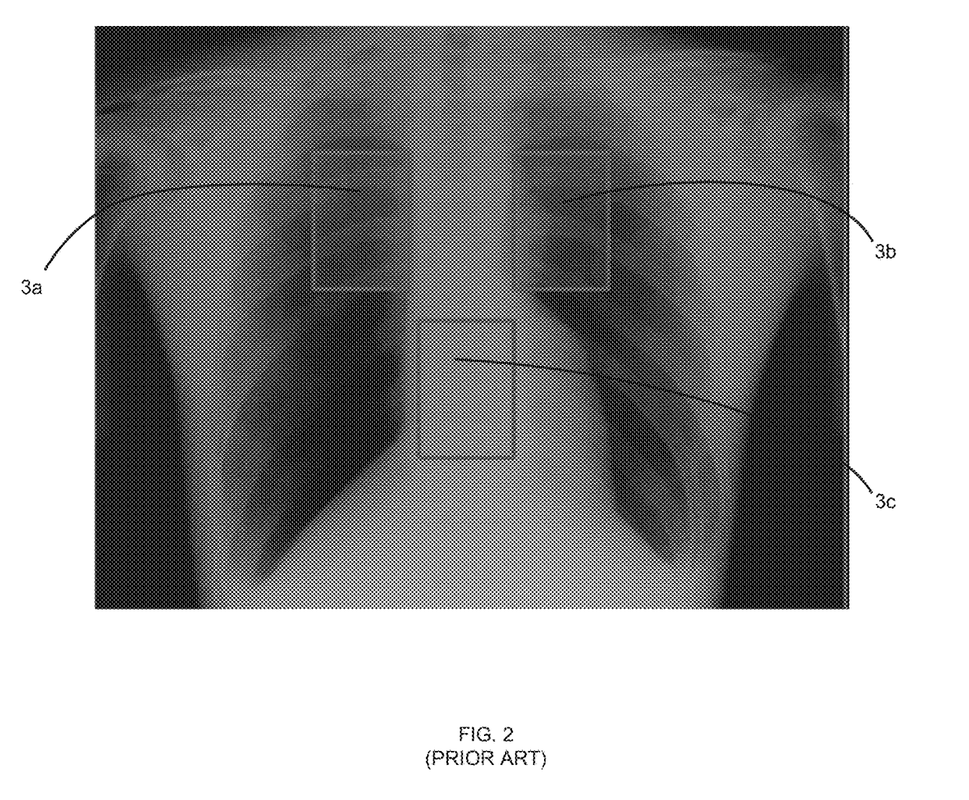
FIG. 2 illustrates AEC sensing regions for chest radiography.

Referring to FIG. 2, in addition to this problem of time scaling, traditional AEC detectors for radiography provide an AEC signal that is proportional to specific regions of the total image, e.g., typical AEC sensing regions 3a, 3b, 3c used for chest radiography.

Figure 3:
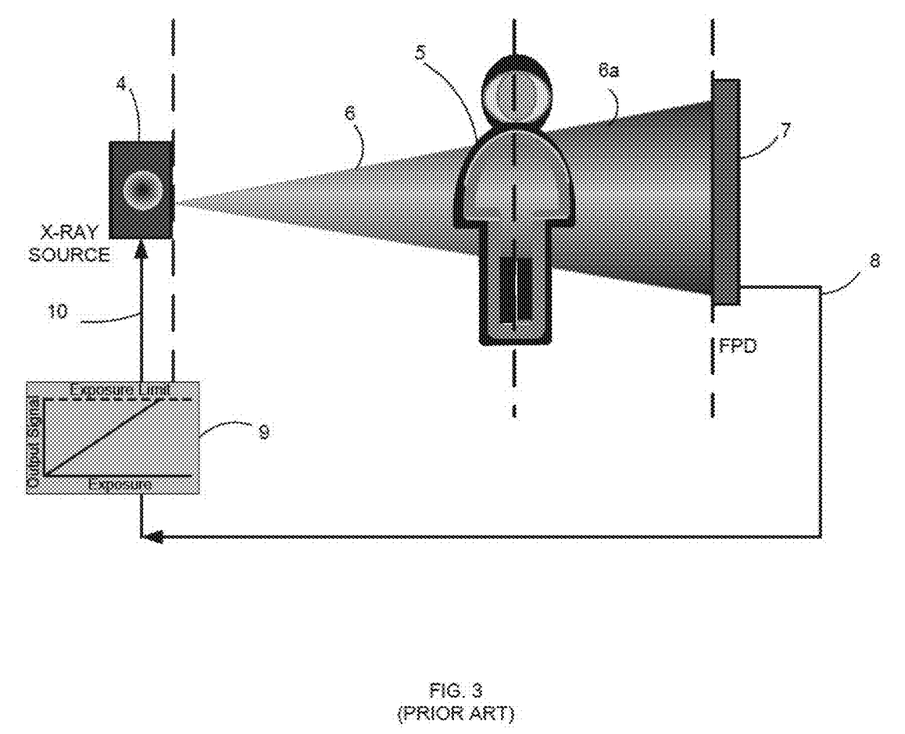
FIG. 3 depicts an x-ray system using a flat panel detector.

Referring to FIG. 3, in a conventional flat panel digital radiography system, an x-ray source 4 irradiates a patient 5 with an x-ray beam 6. The radiation 6a not blocked or absorbed by the patient 5 is received by the flat panel detector 7. Typically, an external AEC detector (not shown) associated with the flat panel detector 7 provides the AEC signal 8, which is monitored by a controller 9 to provide an appropriate x-ray control signal 10 to terminate x-ray emissions when an exposure level sufficient to create a diagnostically useful image has been achieved. While external AEC detectors generally work well, they add significant cost to the overall system. Further, at least two external AEC detectors are often required since, unlike many flat panel detectors, they are not intended to move between table and chest stands, but are built into the x-ray table or chest stand.

SUMMARY

In accordance with the presently claimed invention, an imaging array with integrated circuitry for supporting automatic exposure control and a method for using such an imaging array are provided. One or more electrodes are disposed substantially parallel with at least a portion of the array of pixels forming the imaging array and provide capacitively coupling to at least one photodiode electrode.

In accordance with one embodiment of the presently claimed invention, an imaging array with integrated circuitry for supporting automatic exposure control includes: a plurality of bias lines to convey a bias voltage; a plurality of data lines to convey a plurality of data signals; a plurality of address lines to convey a plurality of address signals; a plurality of pixels disposed among a plurality of rows and a plurality of columns, wherein each pixel includes a photodiode coupled to one of the plurality of bias lines and including first and second photodiode electrodes, a switch transistor including a first switch electrode coupled to the first photodiode electrode, a second switch electrode coupled to one of the plurality of data lines and a control electrode coupled to one of the plurality of address lines; and at least one electrode disposed substantially parallel with at least one portion of the plurality of pixels and capacitively coupled to at least one the first photodiode electrode.

In accordance with another embodiment of the presently claimed invention, a method of monitoring electrical charges accumulating within an imaging array for supporting automatic exposure control includes: accumulating electrical charges within an imaging array that includes a plurality of bias lines to convey a bias voltage, a plurality of data lines to convey a plurality of data signals, a plurality of address lines to convey a plurality of address signals, a plurality of pixels disposed among a plurality of rows and a plurality of columns, wherein each pixel includes a photodiode coupled to one of the plurality of bias lines and including first and second photodiode electrodes, a switch transistor including a first switch electrode coupled to the first photodiode electrode, a second switch electrode coupled to one of the plurality of data lines and a control electrode coupled to one of the plurality of address lines; and capacitively coupling to at least one the first photodiode electrode with at least one electrode disposed substantially parallel with at least one portion of the plurality of pixels.

DETAILED DESCRIPTION

The following detailed description is of example embodiments of the presently claimed invention with references to the accompanying drawings. Such description is intended to be illustrative and not limiting with respect to the scope of the present invention. Such embodiments are described in sufficient detail to enable one of ordinary skill in the art to practice the subject invention, and it will be understood that other embodiments may be practiced with some variations without departing from the spirit or scope of the subject invention.

Throughout the present disclosure, absent a clear indication to the contrary from the context, it will be understood that individual circuit elements as described may be singular or plural in number. For example, the terms "circuit" and "circuitry" may include either a single component or a plurality of components, which are either active and/or passive and are connected or otherwise coupled together (e.g., as one or more integrated circuit chips) to provide the described function. Additionally, the term "signal" may refer to one or more currents, one or more voltages, or a data signal. Within the drawings, like or related elements will have like or related alpha, numeric or alphanumeric designators. Further, while the present invention has been discussed in the context of implementations using discrete electronic circuitry (preferably in the form of one or more integrated circuit chips), the functions of any part of such circuitry may alternatively be implemented using one or more appropriately programmed processors, depending upon the signal frequencies or data rates to be processed. Moreover, to the extent that the figures illustrate diagrams of the functional blocks of various embodiments, the functional blocks are not necessarily indicative of the division between hardware circuitry. Thus, for example, one or more of the functional blocks may be implemented in a single piece of hardware.

As is well known, a flat panel detector 7 can be either an indirect flat panel detector or a direct flat panel detector. As its well-known in the art, an indirect flat panel detector uses a scintillator screen to receive the x-ray radiation and generate visible photons, which are, in turn, captured and converted to electron-hole pairs in a photodiode array. This is contrast to a direct flat panel detector that converts the x-ray photon energy directly to electron-hole pairs.

Figure 4:
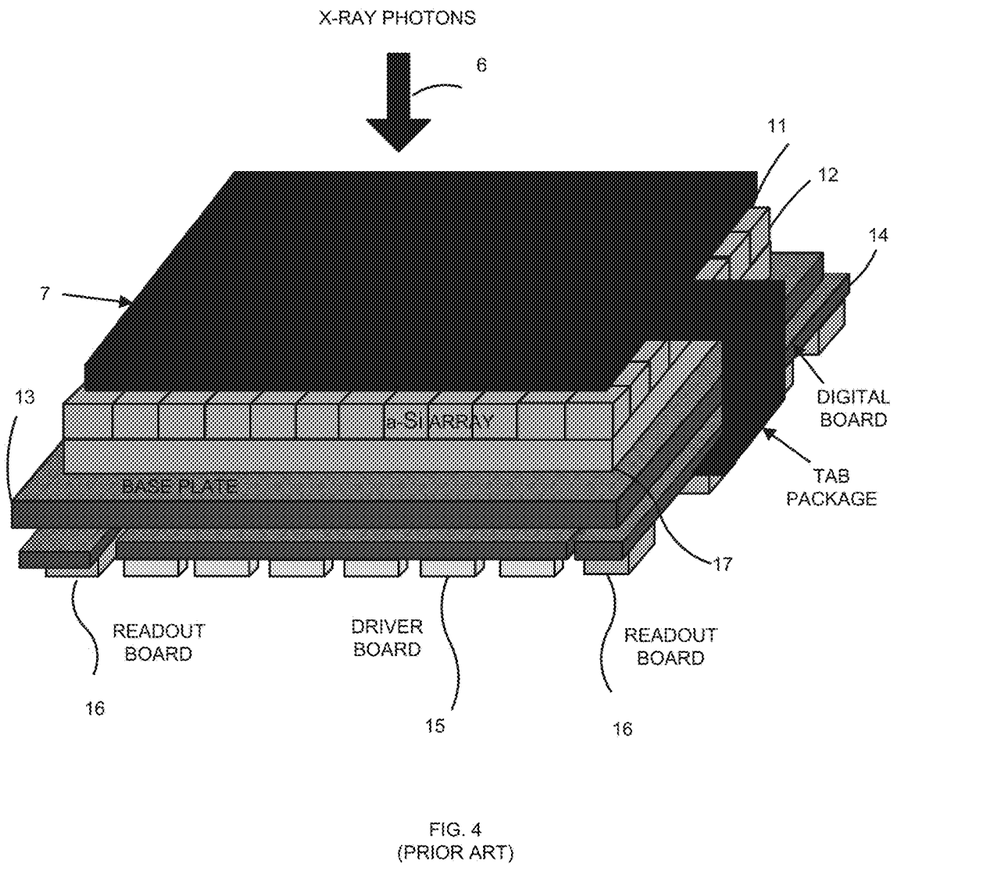
FIG. 4 depicts internal construction of an indirect flat panel detector.

Referring to FIG. 4, a conventional indirect flat panel detector includes the scintillator screen 11, a pixel array 12, a base plate 13, digital circuitry 14, driver circuitry 15 and readout circuitry 16, in accordance with well-known principals and techniques. Typically, the core of the flat panel detector 7 is an amorphous silicon (a-Si) photodiode array 12, which is fabricated on a glass substrate 17 using standard semiconductor processing. While a number of pixel architectures are in use, perhaps used most often is a p-i-n, thin film transistor architecture, in which each pixel includes a thin film transistor (TFT) and a p-i-n photodiode.

Figure 5:
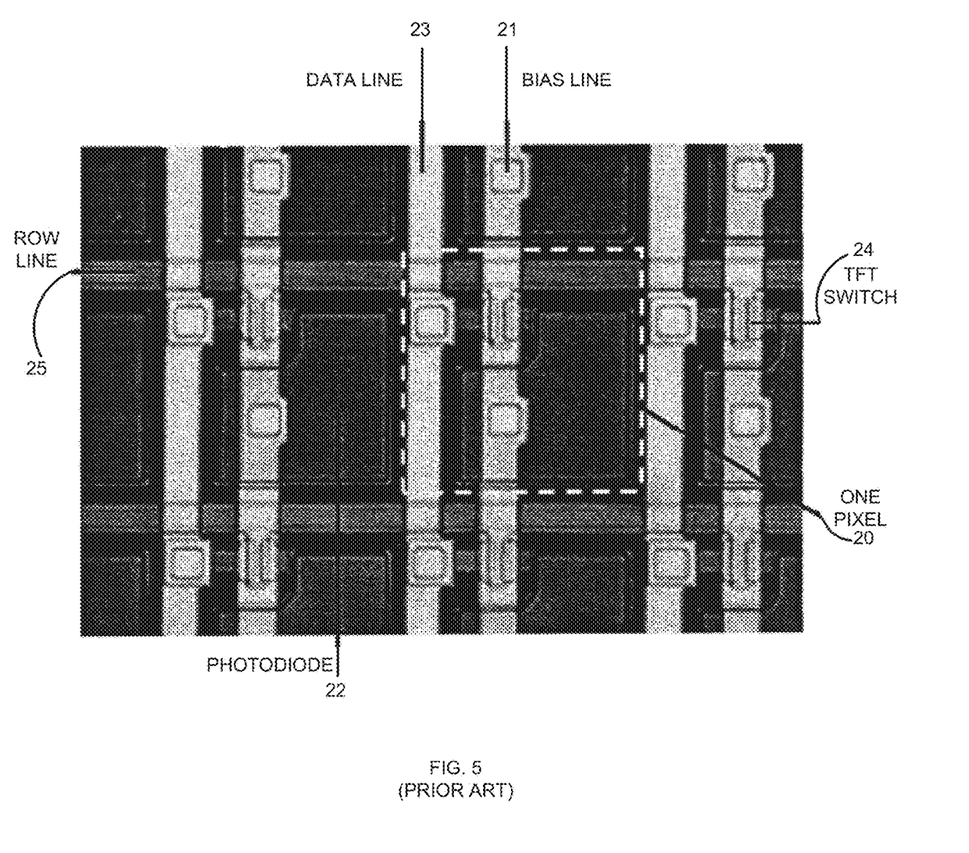
FIG. 5 illustrates a plan view of a portion of a photodiode array.

Referring to FIG. 5, each pixel 20 of such a photodiode array includes the photodiode 22 and TFT Switch 24, which are connected to a bias line 21, a data line 23 and a row, or address, line 25, in accordance with well-known principals. The light sensitive p-i-n photodiode 22 occupies most of the surface area of the array. Its top electrode is typically indium tin oxide (ITO) and allows visible light to penetrate the diode. Further, the top side p-layer of the photodiode is made thin enough to allow most of the visible photons to be absorbed in the thicker intrinsic layer of the photodiode.

Figure 6:
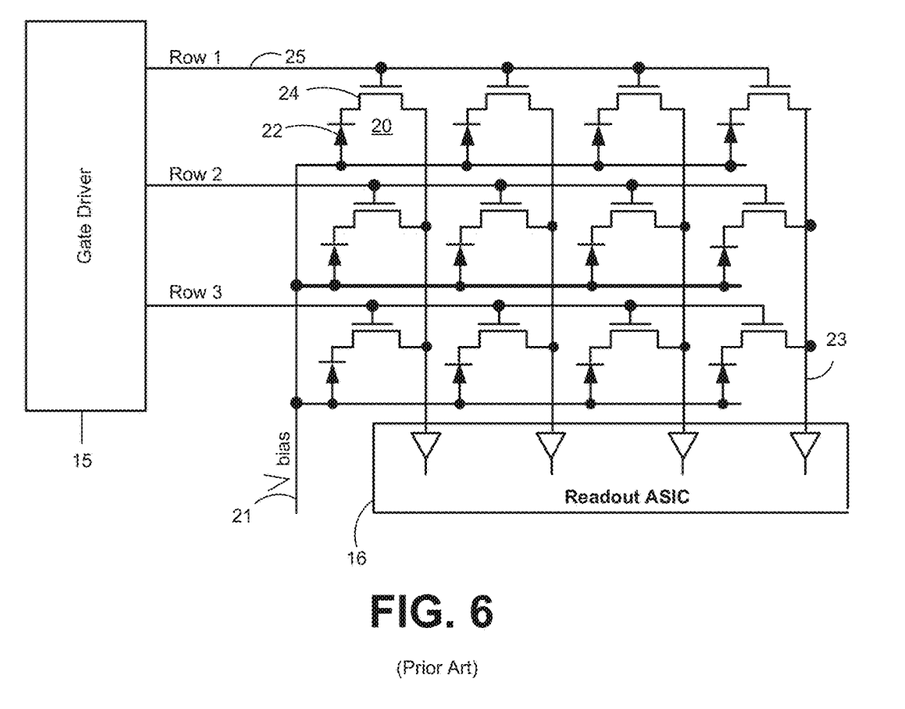
FIG. 6 is a schematic diagram of a photodiode array.

Referring to FIG. 6, electrical operation of such a photodiode array can be understood in accordance with the circuit schematic as shown. As discussed above, each pixel 20 includes a photodiode 22 and TFT switch 24. The gate, or control, electrode of the TFT switch 24 is driven by the row, or address, line 25. The anode of the photodiode 22 is biased by a bias voltage 21 and the output electrode of the TFT switch 24 drives the data line 23. The row, or address, lines 25 are driven by gate driver circuitry 15, and the data lines 23 provide data signals to the readout circuitry 16, all in accordance with well-known principles and techniques.

Figure 7:
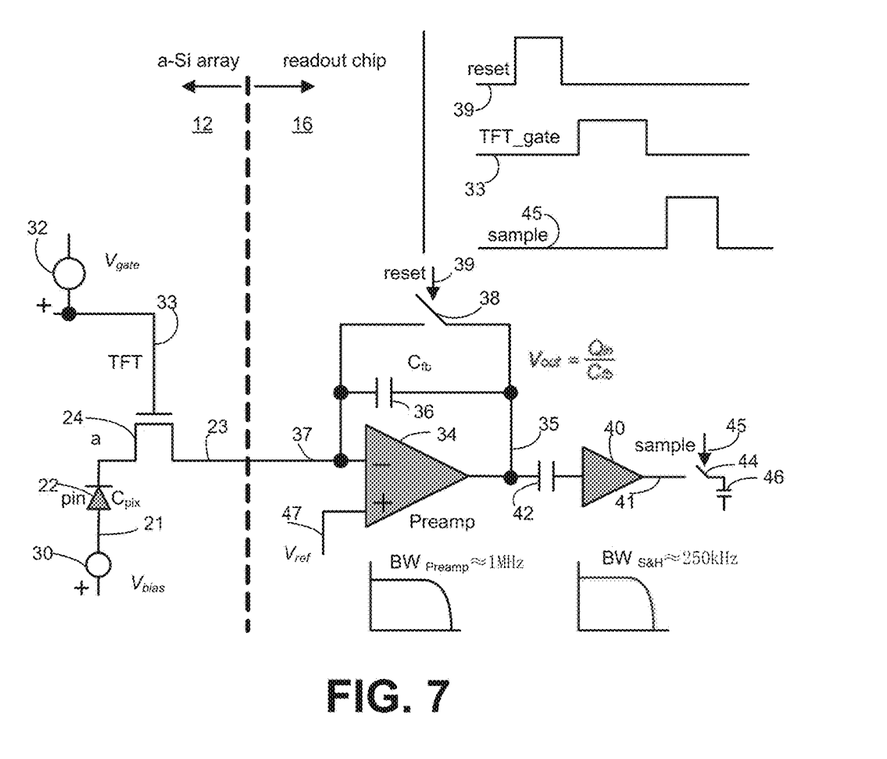
FIG. 7 is a schematic diagram of a pixel and its associated readout circuitry.

Referring to FIG. 7, operation and interaction between the photodiode array 12 and readout circuitry 16 can be better understood. As discussed above, a bias voltage source 30 provides a bias voltage 21 to the anode of the photodiode 22. During an exposure, charges collect within the capacitance of the photodiode, thereby generating a pixel voltage at the node a connecting the photodiode cathode and TFT switch 24. The TFT switch 24 is turned on and off by a control voltage 33 provided by a switch control voltage source 32.

When the TFT switch 24 is turned on, the charges from the photodiode 22 form a current which is converted to a voltage 35 by integration circuitry implemented using a differential amplifier 34 driven by a reference voltage 47, and a feedback capacitance 36, in accordance with well-known principles and techniques. The integrated voltage 35 is conveyed via a coupling capacitor 42 to a voltage amplifier 40, the output voltage 41 of which is sampled by a switch 44 and stored across a capacitance 46, in accordance with well-known principles and techniques.

At the pixel level readout timing is as follows. During integration, the TFT switch 24 is open, or off. Light absorbed by the photodiode 24 creates electron-hole pairs in its intrinsic layer. The internal field of the photodiode under reverse bias separates the electrons and holes, forcing them to opposing electrodes, thereby causing charge to be stored on the capacitance formed in the photodiode. This charge stored on the pixel capacitance causes the voltage on the floating node a to move in a negative direction, thereby reducing the bias across the photodiode 22.

During readout, the TFT switch 24 is closed, or on, thereby connecting node a of the pixel to the data line 23, which is held at a virtual bias potential provided by the reference voltage 47 of the differential amplifier 34. Node a is then discharged onto the data line 23 and into the feedback capacitance 36 of the integration circuitry.

As depicted in the signal timing diagram portion, the feedback capacitance 36 is discharged by a reset switch 38 in accordance with a reset control signal 39. This is followed by the TFT switch 24 being turned on in accordance with its gate, or control, voltage 33 to discharge the pixel photodiode 22. This signal charge is accumulated on the feedback capacitance 36 for conversion to a voltage 35, which, after buffering by the voltage amplifier 40, is sampled by a sampling switch 44 in accordance with a sample control signal 45.

Figure 8:
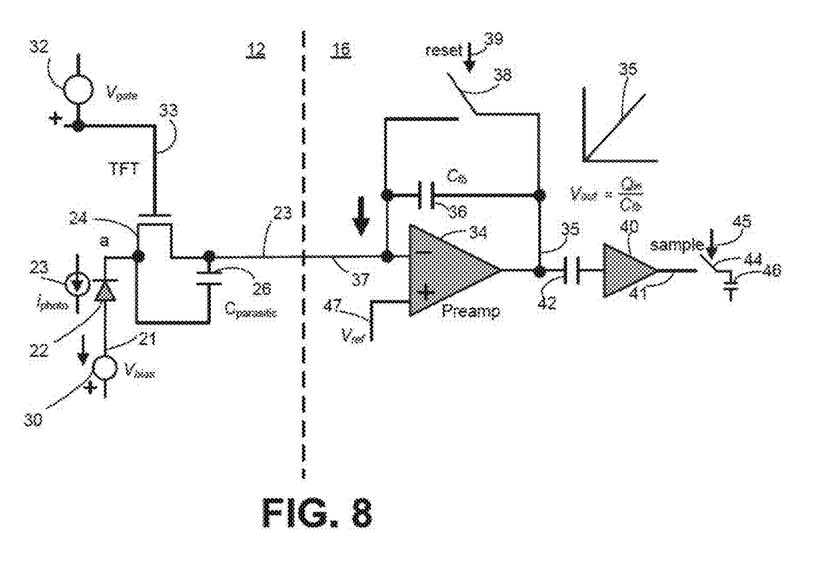
FIG. 8 is a schematic diagram of a pixel and its associated readout circuitry including the parasitic capacitance of the pixel.

Referring to FIG. 8, in accordance with an exemplary embodiment of the presently claimed invention, a parasitic effect present in the normal operation of the flat panel when the x-ray beam is incident during the readout of the frame time is used advantageously. For example, when a pixel is integrating, the TFT switch 24 is turned off. The scintillator light hitting the photodiode 22 creates a photo-generated current in the diode 22. This causes the voltage at node a to move in a negative direction. A parasitic capacitance 26 exists between node a and the data line 23. As a result, the voltage movement at node a is sensed by the readout amplifier 34 (when it is not in reset) due to the coupling effect of the parasitic capacitance 26. Meanwhile, the data line voltage 37 is held at a constant potential 47 due to the operation of the differential amplifier 34. As the voltage at node a changes, so does the voltage across the parasitic capacitance 26. This means that a current must be supplied from the data line 23 to the parasitic capacitance 26 so that the data line voltage 37 remains constant. During readout of the photodiode array 12, every exposed pixel on a given data line 23 contributes to this parasitic signal current.

The signals generated by this parasitic effect appear on a column-by-column basis with no row-dimension information. Accordingly, in accordance with an exemplarily embodiment of the presently claimed invention, an additional layer is introduced on top of the photodiode array where specific regions of this layer will be capacitively coupled to the photo-generated current within the photodiode array below.

Figure 9:
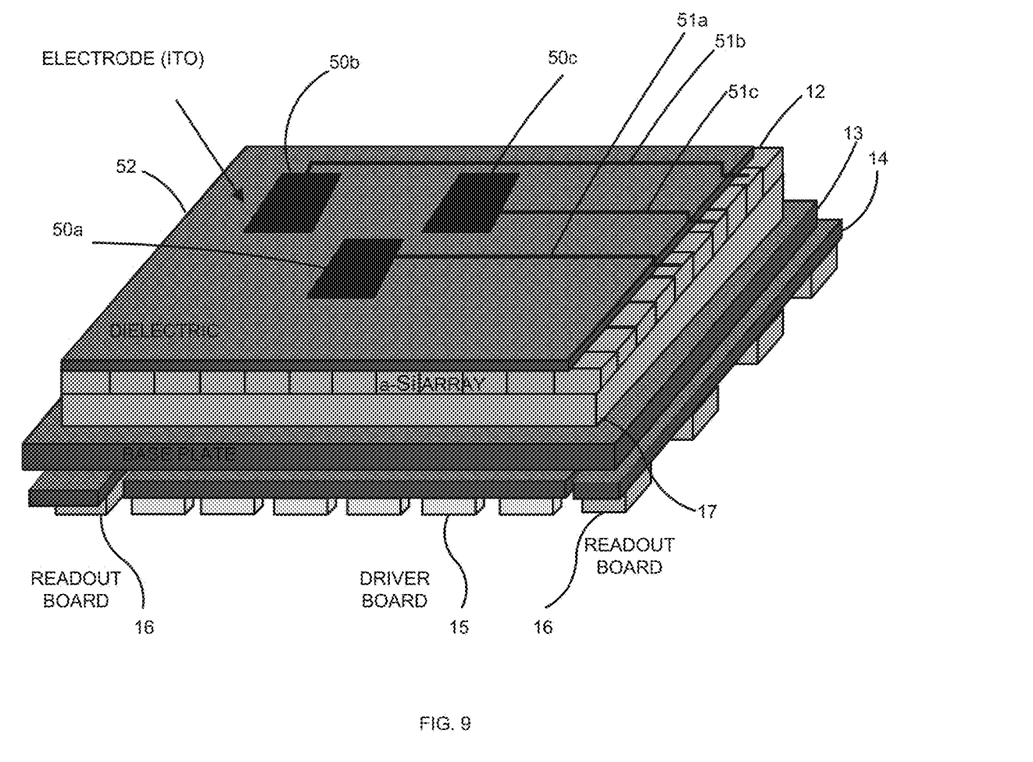
FIG. 9 depicts construction of a flat panel detector supporting AEC in accordance with an exemplary embodiment of the presently claimed invention.

Referring to FIG. 9, in accordance with an exemplary embodiment, such a layer is implemented in the form of a patterned ITO layer, e.g., with ITO regions 50a, 50b, 50c, on top of the final passivation layer 52 to introduce the capacitor electrodes 50a, 50b, 50c and their connections 51a, 51b, 51c to the periphery of the array. These lines 51a, 51b, 51c can make a connection to TAB pads so that the capacitor electrodes can be connected by a passive flex connection to readout circuitry similar to that forming the readout circuitry 16 as discussed above for FIGS. 7 and 8.

This electrode layer 50 can be created during the array fabrication process, since ITO, dielectric and metal layers are available as standard components both the fabrication process.

Figure 13:
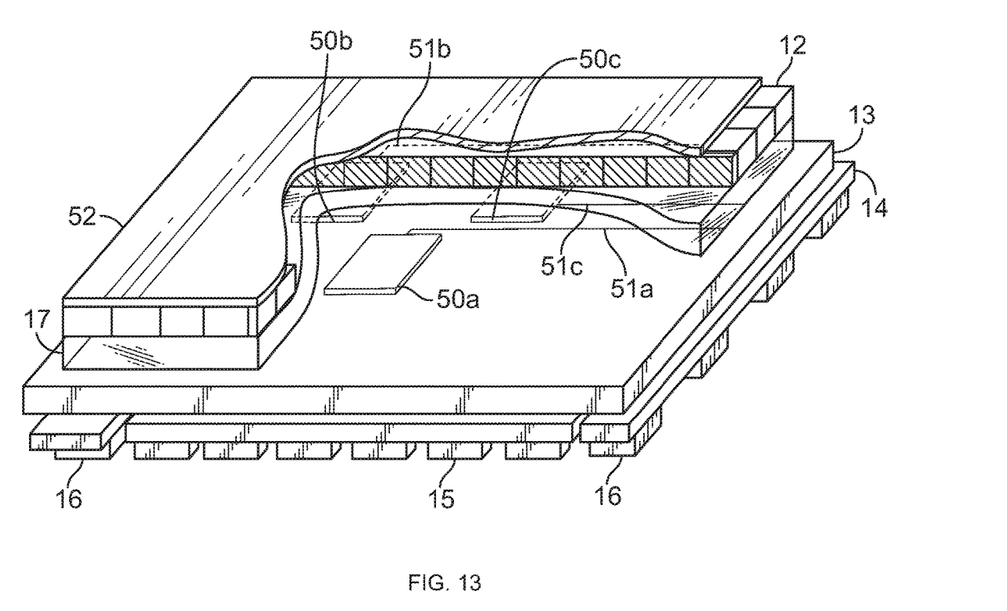

Referring to FIG. 13, in accordance with another exemplary embodiment, the electrodes 50 can be placed below the array 12, e.g., on the back side of its supporting glass substrate 17. Advantages of these embodiment include: such electrodes can be metal (opaque); the electrodes are not screened from the active pixel node by other circuit components; the electrodes need not be fabricated as part of the panel fabrication process, but can be applied to the underside of the glass during the panel assembly process; and connection of the electrodes to circuit boards nearby may be simpler. However, sensitivity of the circuit may be degraded due to the increased distance between the electrode and active pixel node, and the assembly process may require some manual handling.

Figure 10:
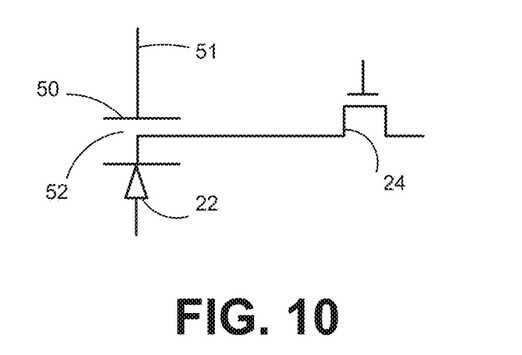
FIG. 10 is a schematic diagram depicting the electrical connection of an AEC electrode in relation to a photodiode of a pixel.

Referring to FIG. 10, it can be seen schematically how the AEC electrodes 50 capacitively couple to an electrode, e.g., the cathode, of the photodiode 22.

Figure 11:
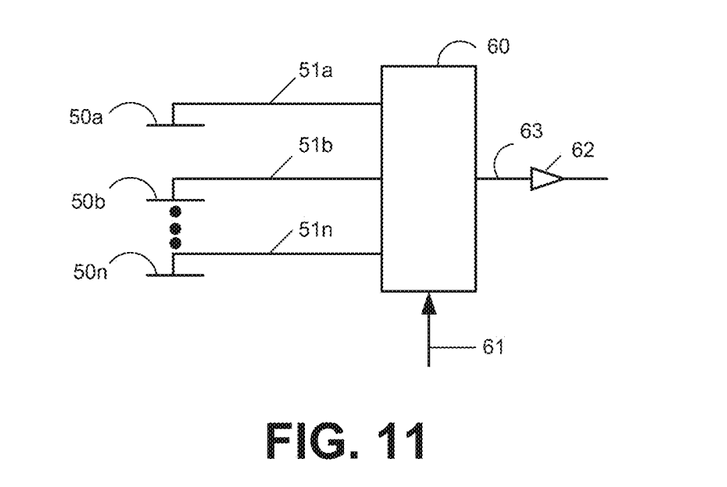
FIG. 11 is a schematic diagram depicting addressing circuitry for an array of AEC electrodes.

Referring to FIG. 11, in accordance with another exemplary embodiment, the AEC electrodes 50 (FIGS. 9 and 10) can be implemented as an array of such electrodes 50a, 50b, . . . , 50n, with their signal lines 51a, 51b, . . . , 51n connected to interface circuitry 60 (e.g., addressing circuitry in the form of multiplexors or switches), which can provide for addressing or accessing AEC signals from one or more desired regions of interest in accordance with a programmable control signal 61. The resulting selected signal 63 can then be further processed, e.g., integrated by charge integration circuitry or amplified by amplifier circuitry 62.

Figure 12:
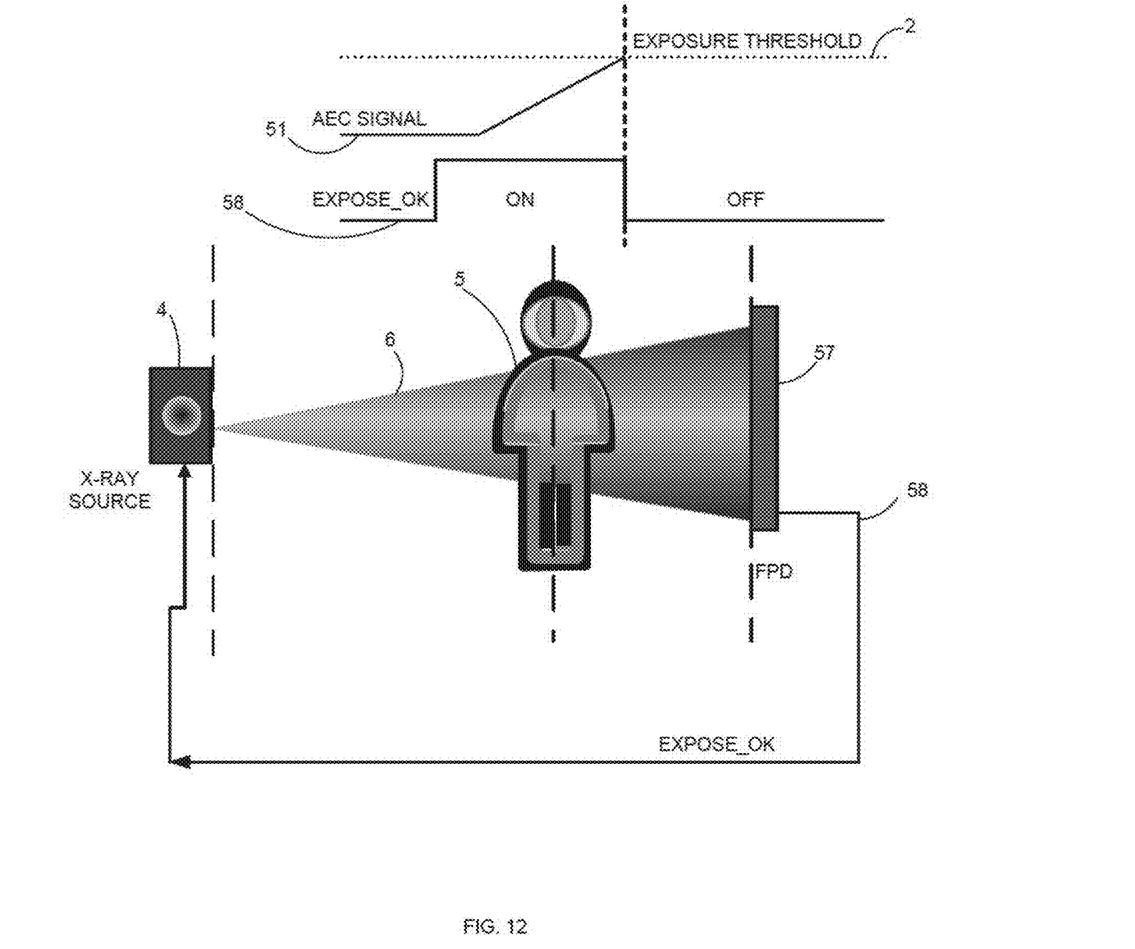
FIG. 12 depicts a radiography system using a flat panel detector supporting AEC in accordance with another exemplary embodiment of the presently claimed invention.

Referring to FIG. 12, the AEC signal voltage is traditionally an analog voltage supplied to a threshold circuit that indicates to the radiation source 4 when to terminate the x-ray pulse 6. Such an analog voltage could be delivered from the flat panel display 57 as discussed above. However, in accordance with another exemplary embodiment, some flat panel displays 57 provide what is referred to as an "Expose OK" signal 58. This signal 58 is a binary signal that defines the "on" time in which the x-ray beam can be delivered to the panel 57. Generally, this corresponds to the integration phase of the panel read out cycle. Accordingly, this signal 58 also identifies the "off" state, the beginning of which is when the accumulated AEC signal 51 measured in the panel 57 has exceeded the predefined threshold. Accordingly, the "off" state of this signal 58 can be used to terminate the x-ray exposure.

Various other modifications and alternations in the structure and method of operation of this invention will be apparent to those skilled in the art without departing from the scope and the spirit of the invention. Although the invention has been described in connection with specific preferred embodiments, it should be understood that the invention as claimed should not be unduly limited to such specific embodiments. It is intended that the following claims define the scope of the present invention and that structures and methods within the scope of these claims and their equivalents be covered thereby.

What is claimed is:

1. An apparatus including an imaging array for supporting automatic exposure control, comprising:
   a support substrate with opposing first and second substrate surfaces, wherein at least a portion of said second substrate surface is planar and includes an electrode region and a non-electrode region;
   integrated circuitry separate from said support substrate, disposed on said first substrate surface and including
   a plurality of bias lines to convey a bias voltage;
   a plurality of data lines to convey a plurality of data signals;
   a plurality of address lines to convey a plurality of address signals;
   a plurality of pixels disposed among a plurality of rows and a plurality of columns, wherein each pixel includes
      a photodiode coupled to one of said plurality of bias lines and including first and second photodiode electrodes, and
      a switch transistor including a first switch electrode coupled to said first photodiode electrode, a second switch electrode coupled to one of said plurality of data lines and a control electrode coupled to one of said plurality of address lines; and
   at least one electrode disposed in said electrode region of said second substrate surface, substantially parallel with at least one portion of said plurality of pixels and capacitively coupled to at least one said first photodiode electrodes;
   wherein electrodes are not disposed in said non-electrode region, and said electrode and non-electrode regions are mutually coplanar.

2. The apparatus of claim 1, wherein said at least one electrode comprises a plurality of planar conductors.

3. The apparatus of claim 1, wherein said at least one electrode comprises a patterned layer of electrically conductive material.

4. The apparatus of claim 1, wherein said at least one electrode comprises a plurality of electrodes disposed in an array, and further comprising:
   receiving circuitry; and
   interface circuitry coupled between said plurality of electrodes and said receiving circuitry to selectively convey electrical charges from one or more portions of said plurality of electrodes to said receiving circuitry.

5. The apparatus of claim 1, further comprising amplifier circuitry coupled to said at least one electrode.

6. The apparatus of claim 1, further comprising charge integration circuitry coupled to said at least one electrode.

7. A method of monitoring electrical charges accumulating within an imaging array for supporting automatic exposure control, comprising:

accumulating electrical charges within an imaging array that includes
a plurality of bias lines to convey a bias voltage,
a plurality of data lines to convey a plurality of data signals,
a plurality of address lines to convey a plurality of address signals,
a plurality of pixels disposed among a plurality of rows and a plurality of columns, wherein each pixel includes
a photodiode coupled to one of said plurality of bias lines and including first and second photodiode electrodes, and
a switch transistor including a first switch electrode coupled to said first photodiode electrode, a second switch electrode coupled to one of said plurality of data lines and a control electrode coupled to one of said plurality of address lines;
supporting said integrated circuitry with separate substrate having opposing first and second substrate surfaces with said integrated circuitry disposed on said first substrate surface, wherein at least a portion of said second substrate surface is planar and includes an electrode region and a non-electrode region; and
capacitively coupling to at least one said first photodiode electrode with at least one electrode disposed in said electrode region of said second substrate surface and substantially parallel with at least one portion of said plurality of pixels;
wherein electrodes are not disposed in said non-electrode region, and said electrode and non-electrode regions are mutually coplanar.

8. The method of claim 7, wherein said capacitively coupling to at least one said first photodiode electrode with at least one electrode disposed on said planar portion of said second substrate surface and substantially parallel with at least one portion of said plurality of pixels comprises capacitively coupling with a plurality of planar conductors.

9. The method of claim 7, wherein said capacitively coupling to at least one said first photodiode electrode with at least one electrode disposed on said planar portion of said second substrate surface and substantially parallel with at least one portion of said plurality of pixels comprises capacitively coupling with a patterned layer of electrically conductive material.

10. The method of claim 7, wherein:
said capacitively coupling to at least one said first photodiode electrode with at least one electrode disposed on said planar portion of said second substrate surface and substantially parallel with at least one portion of said plurality of pixels comprises capacitively coupling with a plurality of electrodes disposed in an array; and
said method further comprises selectively conveying electrical charges from one or more portions of said plurality of electrodes to receiving circuitry.

* * * * *